United States Patent
Lieber et al.

(10) Patent No.: US 10,426,398 B2
(45) Date of Patent: Oct. 1, 2019

(54) METHODS FOR OPTICALLY MEASURING MUSCLE SARCOMERE LENGTH

(71) Applicant: REHABILITATION INSTITUTE OF CHICAGO, Chicago, IL (US)

(72) Inventors: Richard L. Lieber, Chicago, IL (US); Stojan Radic, San Diego, CA (US); Kevin Young, San Diego, CA (US)

(73) Assignee: REHABILITATION INSTITUTE OF CHICAGO, Chicago, IL (US)

( * ) Notice: Subject to any disclaimer, the term of this patent is extended or adjusted under 35 U.S.C. 154(b) by 677 days.

(21) Appl. No.: 14/872,906

(22) Filed: Oct. 1, 2015

(65) Prior Publication Data
US 2017/0049381 A1    Feb. 23, 2017

Related U.S. Application Data
(60) Provisional application No. 62/058,370, filed on Oct. 1, 2014.

(51) Int. Cl.
| | | |
|---|---|---|
| *A61B 5/00* | (2006.01) | |
| *A61B 5/107* | (2006.01) | |

(52) U.S. Cl.
CPC .......... *A61B 5/4519* (2013.01); *A61B 5/0075* (2013.01); *A61B 5/0084* (2013.01); *A61B 5/1076* (2013.01); *A61B 5/1079* (2013.01); *A61B 2505/05* (2013.01)

(58) Field of Classification Search
CPC . A61B 2505/05; A61B 5/0075; A61B 5/0084; A61B 5/1076; A61B 5/1079; A61B 5/4519
See application file for complete search history.

(56) References Cited

U.S. PATENT DOCUMENTS
4,693,606 A * 9/1987 Podolsky ........... G01N 15/0211
                                                      33/706

OTHER PUBLICATIONS
Lieber et al, "In Vivo Measurement of Human Wrist Extensor Muscle Sacromere Length Changes", Journal of Neurophysiology, vol. 71, No. 3, Mar. 1994 (Year: 1994).*

* cited by examiner

*Primary Examiner* — Ruth S Smith
(74) *Attorney, Agent, or Firm* — Drinker Biddle & Reath LLP (57) ABSTRACT

Methods and systems for measuring muscle sarcomere length are disclosed. In an embodiment, a method comprises illuminating a set of muscle fibers with electromagnetic radiation, measuring an intensity of the electromagnetic radiation as reflected from the muscle fibers, the measuring occurring as a function of wavelength, determining wavelengths corresponding to maximums of reflected intensity, and correlating the determined wavelengths with respective muscle sarcomere lengths. In an embodiment, a system comprises an illumination source system for illuminating the set of muscle fibers with electromagnetic radiation, and an analyzer for measuring the intensity of the electromagnetic radiation as reflected from the muscle fibers.

7 Claims, 9 Drawing Sheets

METHODS FOR OPTICALLY MEASURING MUSCLE SARCOMERE LENGTH

CROSS REFERENCE TO RELATED APPLICATIONS

This application claims the priority benefit of U.S. Provisional Patent Application No. 62/058,370 filed on Oct. 1, 2014, which is herein incorporated by reference.

STATEMENT REGARDING FEDERALLY SPONSORED RESEARCH OR DEVELOPMENT

This invention was made with government support under A9028R awarded by the Department of Veterans Affairs and R24 HD050837 awarded by the National Institutes of Health. The government has certain rights in the invention.

FIELD

The disclosure relates to the optical measurement of muscle length.

BACKGROUND

Sarcomeres, the functional units of contraction in striated muscle, are composed of an array of interdigitating protein filaments. Direct interaction between overlapping filaments generates muscular force, which produces animal movement. When filament length is known, sarcomere length successfully predicts potential force, even in whole muscles that contain billions of sarcomere units. Inability to perform in vivo sarcomere measurements with sub-micrometer resolution is a long-standing challenge in the muscle physiology field and has hampered studies of normal muscle function, adaptation, injury, aging, and disease, particularly in humans.

Laser diffraction, biopsy clamps, and two-photon microscopy have been used in prior attempts to measure in vivo sarcomere length, but each has limitations. Laser diffraction and biopsy clamps are restricted to surgical settings, limiting access to muscle types and patients available for study. Two-photon microscopy is an emerging technique which measures sarcomere length through a microendoscopic probe. This type of procedure allows for greater access to muscles and patient populations. Two-photon microscopy, however, is a point scanning method which by its nature struggles with acquisition speed, measurement depth, and motion artifacts.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

Methods and systems for measuring muscle sarcomere length are disclosed. In an embodiment, a method of measuring muscle sarcomere length is disclosed that comprises illuminating a set of muscle fibers with electromagnetic radiation, measuring an intensity of the electromagnetic radiation as reflected from the muscle fibers, the measuring occurring as a function of wavelength, determining wavelengths corresponding to maximums of reflected intensity, and correlating the determined wavelengths with respective muscle sarcomere lengths. The illuminating may include illuminating with a supercontinuum source and/or illuminating in a collinear fashion. The illuminating and measuring may be performed by a resonant reflection spectroscopy system. The method may further comprise determining a single measured resonant wavelength falling in a wavelength band.

In an embodiment, a system for measuring muscle sarcomere length is disclosed. The system may comprise a resonant reflection spectroscopy system, including an illumination source for illuminating a set of muscle fibers with electromagnetic radiation; means for measuring an intensity of the electromagnetic radiation as reflected from the muscle fibers, and to determined wavelengths corresponding to maximums of reflected intensity; and a computing environment configured to correlate the determined wavelengths with a muscle sarcomere length. The illumination source may be a supercontinuum source. The illumination may be configured to deliver electromagnetic radiation in a collinear fashion.

In an embodiment, a system is disclosed that comprises an illumination source system for illuminating a set of muscle fibers with electromagnetic radiation, and an analyzer for measuring the intensity of the electromagnetic radiation as reflected from the muscle fibers. The system may comprise a supercontinuum source. The illumination source system may further comprise a highly nonlinear fiber. The illumination source system may further comprise a probe for insertion into the set of muscle fibers. The system may further comprise an optical circulator. The supercontinuum source, the highly nonlinear fiber, the probe, the optical circulator, and the analyzer may be positioned such that during the system's operation, the electromagnetic radiation passes through the fiber, into the optical circulator, and through the probe, and the reflection of the electromagnetic radiation from the set of muscle fibers passes through the probe, into the optical circulator, and to the analyzer. The illumination source may be configured to deliver electromagnetic radiation in a collinear fashion.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

DETAILED DESCRIPTION

Various embodiments meet the needs of the above in several ways. In particular, resonant reflections from sarcomeres are wavelength-dependent and can reveal protein structural information through low-power resonant reflection spectroscopy (RRS).

Thus, systems and methods according to various embodiments allow the measurement of muscle sarcomere length minimally invasively in vivo. This optical technique measures sarcomere length by collinearly illuminating the muscle fiber and measuring reflectance as a function of wavelength. In an embodiment, the technique involves the measurement of multiple resonant reflections that are uniquely defined by Fourier decomposition of the sarcomere protein spatial framework. Maximum reflections occur for wavelengths that satisfy the Bragg equation (termed "Bragg wavelengths"), which relates the optical wavelength to sarcomere length.

Various embodiments facilitate one or more of the following features: The optical scheme described is less invasive and faster than current techniques of measuring in vivo sarcomere length, and allows measurement of sarcomere length with sub micrometer resolution. Muscle dissection is not required since the measured wavefront is reflected rather than transmitted. While implementations of the techniques described herein may be widely applied, one use is in in vivo measurement of sarcomere length during hand surgery. Other features will be understood from the description that follows, including the figures and claims.

Systems and methods according to present disclosure allow the measurement of muscle sarcomere length minimally invasively in vivo. In various embodiments, the systems and methods measure sarcomere length by collinearly illuminating the muscle fiber and measuring reflectance as a function of wavelength. Maximum reflections occur for wavelengths that satisfy the Bragg equation, which relates the optical wavelength to sarcomere length. RRS offers a potential breakthrough for in vivo sarcomere length data collection because it is not restricted by the same fundamental limitations as current techniques. In various embodiments, using the techniques presented here, the resonant reflections that arise from muscle sarcomeres were accurately predicted. Notably, it can be demonstrated that sarcomere lengths measured by RRS match those measured by traditional LD.

In one implementation, and to circumvent the limitations of laser diffraction in the measurement of sarcomere length, muscle fibers may be illuminated, e.g., collinearly, using broad polychromatic illumination to transform sarcomere structure information into the optical frequency domain. This may be accomplished in RRS by measuring intensity of resonant reflections across optical wavelengths (FIG. 1B), rather than measuring intensity of a spatial diffraction pattern, as in LD (see FIG. 1A). Using the optical frequency domain allows illumination and reflected light to traverse the same path, enabling the use of the smallest minimally-invasive needle probes that have been demonstrated for in vivo optical-signal collection in muscle tissue.

Figure 1A:
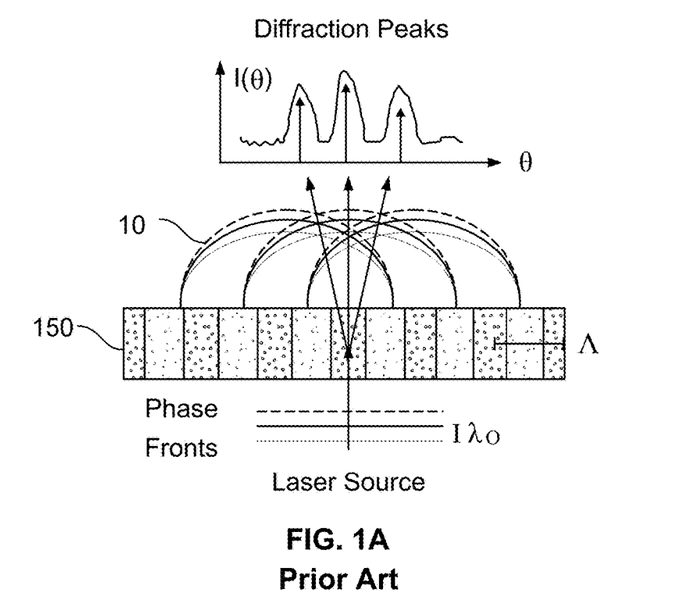
FIGS. 1A and 1B illustrate how sarcomere periodicity and illumination geometry determine optical signals.
Figure 1B:
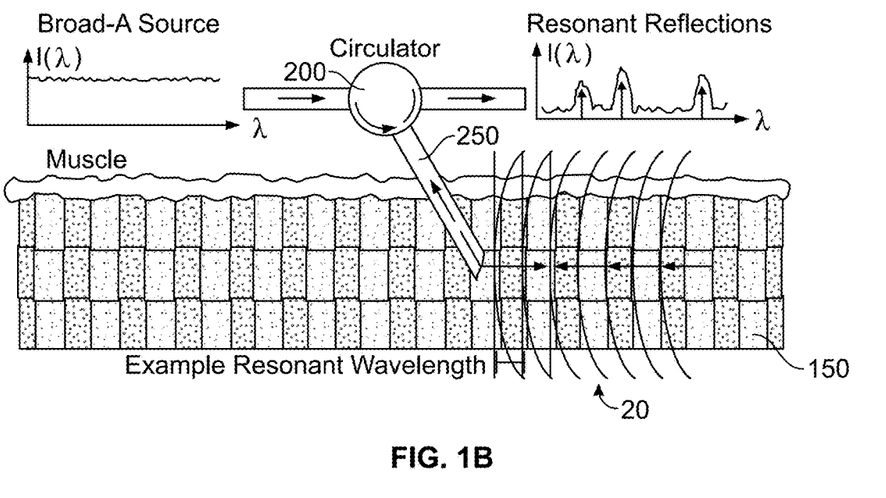

In more detail, FIGS. 1A and 1B illustrate how sarcomere periodicity and illumination geometry determine optical signals. In FIG. 1A, it is seen that a traditional laser diffraction method transforms sarcomere length ($\Lambda$) of a thin muscle sample into the spatial frequency domain through spatial diffraction, though a spatially-encoded signal requires highly invasive surgical settings to measure sarcomere length in vivo. Lines 10 represent the phase fronts of a laser source with wavelength $\lambda_0$. In contrast, and referring to FIG. 1B, resonant reflection spectroscopy transforms sarcomere periodicity into the optical frequency domain through selectively reflected signals, allowing source and signal to be directed through a single minimally invasive fiber optic probe. A broad wavelength source (such as the supercontinuum source 400, described below in conjunction with FIG. 4A) provides optical pulses to a circulator 200, which are transmitted through a probe 250 for reflection into the muscle 150. For clarity, the phase fronts shown are in lines 20 from only the 4th order resonant reflection. The reflected light is returned back through the probe 250 to the circulator, and transmitted for further analysis of resonant reflections (such as to the analyzer 300, described below in conjunction with FIG. 4A).

Resonant reflections occur when individual reflections originating from throughout a periodic structure constructively interfere. To a first approximation, Bragg's law, also called the Bragg resonance condition, determines which optical wavelengths will resonantly reflect from a periodic structure. Under co-linear illumination, Bragg's law states:

$$\lambda_m = \frac{2n_a \Lambda}{m} \quad (1)$$

Where $\lambda_m$ is the resonant wavelength for resonant order m; $n_a$ is the average refractive index; and $\Lambda$ is the structure period. This expression directly links the illumination wavelengths (that will resonate within the sarcomere protein structure and reflect) to sarcomere length modeled as $\Lambda$.

Bragg's law determines the resonant wavelengths, whereas Fourier decomposition of the underlying refractive index profile determines the reflection efficiency of all reflections. Based on the refractive index profile model used here, Fourier decomposition of a sarcomere is a superposition of four distinct protein regions:

$$n(z) = n_a + \sum_{r=1}^{4} \sum_m \alpha_{r,m} \cos(2\pi m z / \Lambda) \quad (2)$$

where $\alpha_{r,m}$ is the Fourier coefficient of region r and order m; and z is distance along the long axis of sarcomeres. Each region contributes to the refractive index and is prescribed by a pulse wave, so Fourier coefficients are described by:

$$|a_{r,m}| = \frac{2A_r}{m\pi} \sin(m\pi L_r / \Lambda) \quad (3)$$

where $A_r$ is the region specific index of refraction contribution; and Lr is the region length. Efficiency of a resonant reflection is proportional to the sum of Fourier coefficients of its harmonic order, m. These equations have several implications that are seen in plots of reflection efficiency generated by rigorous coupled wave analysis (RCWA).

In many optical applications, only fundamental resonant reflections ($\lambda_1$) are measured or studied. However, since sarcomere length varies by more than a factor of two, locating a single resonant wavelength in a spectrum of reflected light does not necessarily enable solving for sarcomere length because the resonance may originate from neighboring harmonic orders. Consequently, a wide spectrum that crosses at least two resonant orders is needed to measure a sufficient spectral fingerprint to uniquely calculate sarcomere length. Importantly, this statement is different than claiming two resonant reflections are required. For example, the $4_{th}$, $5_{th}$, and $6_{th}$ orders are located in the wavelength range 1 μm to 2 μm and sarcomere length range 2.7 μm to 2.8 μm, but the $5_{th}$ and $6_{th}$ orders reflection intensity have disappeared (see, e.g., FIGS. 2B-D). So, sarcomere length of 2.75 μm is predicted to yield a single resonant reflection using RRS. Still, this fingerprint is unique to this sarcomere length and wavelength range, and so sarcomere length can be calculated with confidence from a single measured resonant wavelength falling in this wavelength band.

Figure 2A:
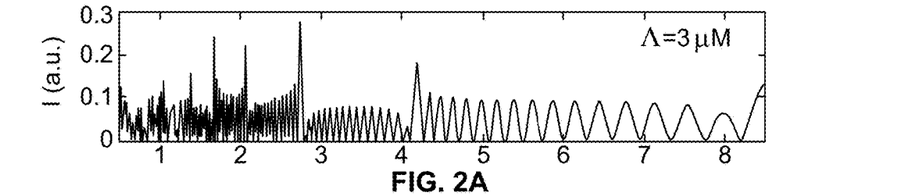
FIG. 2A illustrates expected reflection efficiency from 3 micrometer sarcomeres generated by numerical simulations.

FIG. 2A plots expected reflection efficiency as a function of illumination wavelength for sarcomere length 3.0 μm. The first resonant order, where m=1, is satisfied at approximately 8.5 μm; 8.5 μm is the first resonant wavelength, $\lambda_1$. $\lambda_2$ is approximately 4.2 μm and satisfies the next resonant order, m=2. Note, different resonant orders are not exactly harmonic periods, and this is caused by fine details in the sarcomere index profile. Myosin filament and m-line regions are out-of-phase with actin filament and z-band regions, leading to interference with the net superposition of waves giving slightly shifted peaks. FIG. 2A illustrates a spectral fingerprint unique to this sarcomere length.

Therefore, in an embodiment, a light source with a sufficiently broad and powerful bandwidth may be used to reflect light from muscle or other structure in order to detect multiple resonant orders, and so distinguish structure length on the basis of the detected resonant frequencies. In an embodiment, the supercontinuum source 400 provides a bandwidth that is sufficiently broad and powerful so that when it is reflected against muscle 150, the resonant wavelengths are distinguishable from a muscle of one length in comparison to muscles of other lengths.

Resonant orders that have weak reflections satisfy this requirement if at least one resonant order is measurable for all sarcomere lengths. On one hand, higher orders cover a smaller wavelength range, enabling more orders to be measured. On the other hand, higher orders are affected more significantly by sarcomere inhomogeneity and length changes (see, e.g., FIG. 2B-E). To balance these trade-offs, the system described herein targeted the $4_{th}$, $5_{th}$, and $6_{th}$ orders for experimental measurement by utilizing a supercontinuum source with a wavelength range 1.25 μm (1250 nm) to 2.05 μm (2050 nm). In an embodiment, the difference between the lower end and the upper end of the wavelength range of a supercontinuum source may be 0.8 μm (800 nm). It should be understood that other wavelength ranges may be used instead, depending on the nature of the muscle to be measured, the resonant orders to be targeted, and/or other appropriate factors as would be apparent to one of ordinary skill in the art after reading this application.

Figure 4A:
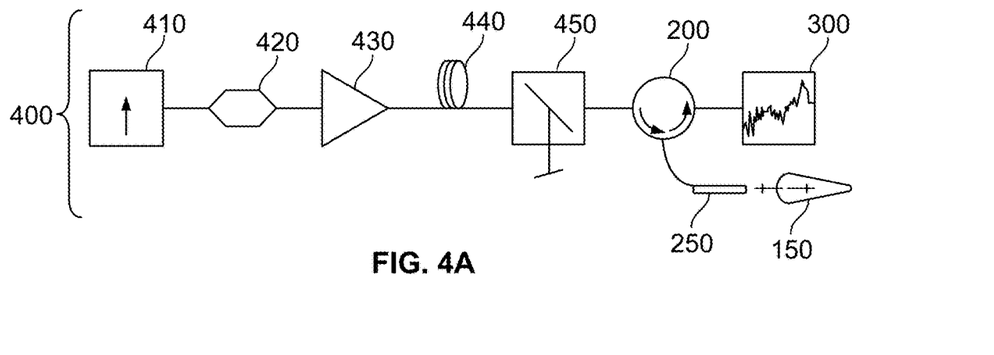
FIGS. 4A-4B illustrate a schematic of a supercontinuum spectroscopic system and its output before and after wavelength division multiplexing.
Figure 4B:
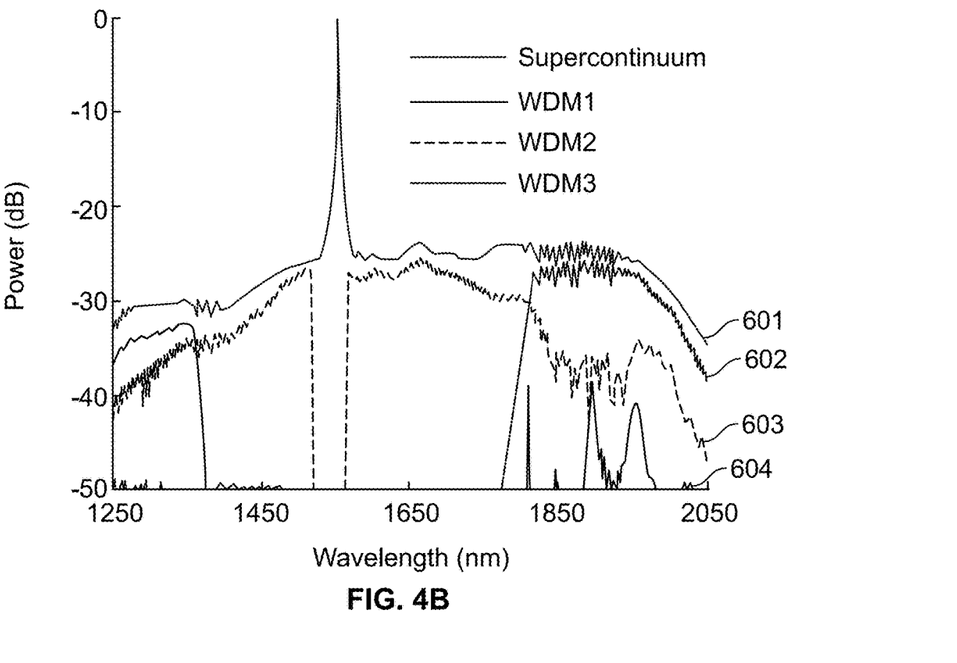

A supercontinuum spectroscopic system 400 may be employed to generate broad optical spectra for reflection upon the muscle 150, in order to determine resonant wavelengths that may be compared against the expected resonant wavelengths for muscles of various lengths, in order to determine the length of sarcomeres in the muscle 150. The supercontinuum spectroscopic system 400 may comprise resonant reflection capabilities. FIG. 4A illustrates a schematic of the supercontinuum spectroscopic system 400. A laser source 410 provides an optic source for the system 400. The laser source 410 may be selected on the basis of its ability to match the zero dispersion wavelength of the highly nonlinear fiber 440 (discussed below), the wavelength of light the laser source 410 is capable of producing, and/or the power of the laser source 410. For example, the laser source 410 may comprise an infrared laser. For example, the laser may be a tunable laser, such as the HP 81684 tunable laser (Palo Alto, Calif.). Light from the laser source 410 passes through a modulator 420 such as a Mach-Zehnder modulator 420. The modulator 420 is used to convert light from the laser source 410 into optical pulses. The optical pulses may be sent to an amplifier 430, for optical amplification to 1 W power or another appropriate amplification. In an embodiment, the optical pulses have a sufficient power, so that when the light is reflected against the muscle 150 in order for the higher order resonant wavelengths to become apparent during analysis (see below). The amplified optical pulses may be sent into highly nonlinear fiber (HNLF) 440. The fiber 440 may be of the kind offered by Sumitomo Electronics, Japan and may have a 1550 nm zero dispersion wavelength. The length of the fiber 440 may be selected to increase the interaction length of the optical pulses. In an embodiment, the length of the fiber 440 may be 280 meters. The pulse duration and the repetition rate may be adjusted by the modulator 420. Center wavelength, pulse duration, and repetition rate may be determined by an optimization wherein the relevant outcome parameters are the amplification of the optical pulses and the minimization of noise produced by amplification. In an embodiment, the raw supercontinuum spectrum at the output of the fiber 440 may span 800 nm with total power in excess of 500 mW. Three wavelength division multiplexers (WDMs) 450 may be used to divide the supercontinuum spectrum produced from the fiber 440 into three wavelength bands. Each band used may have final output power less than 15 mW and 3 dB flatness. FIG. 4B displays a graph of the optical spectrum generated using pulse characteristics of a 1553.4 nm center wavelength for the laser source 410, a 25 ns pulse duration, and 1 MHz repetition rate. The optical spectrum shown is the spectrum 601, the spectrum 604 from the first multiplexer 450, the spectrum 603 from the second multiplexer 450, and the spectrum 602 from the third multiplexer 450.

In an embodiment, to measure sarcomere length by resonant reflection spectroscopy, the wavelength bands from the multiplexers 450 may pass into an optical circulator 200 and through an optical probe 250 into the muscle 150. As shown in FIG. 1B, the optical circulator 200 only permits light propagation to forward ports. Light from the optical circulator 200 passes into an optical probe 250. In an embodiment, the probe 250 may be collinearly aligned to the muscle 150, such that sarcomeres close to the middle of the muscle 150 are measurable by RRS.

In order to determine whether muscle 150 would appropriately reflect a supercontinuum spectrum, an experiment was conducted on animal tissue. In this experiment, whole hind limbs were collected from euthanized mice and rabbits sacrificed for other research. Limbs were pinned to cork board and chemically fixed in 10% formalin for two days. Each sample was rinsed and stored in phosphate-buffered saline. Whole tibialis anterior (TA) and extensor digitorum longus (EDL) muscles (n=6) were collected. Three small subsamples were microdissected at the middle third from each whole muscle for sarcomere length measurement by laser diffraction. Then, muscles were cut in half at approximately 15 degrees from normal. This facilitated coupling between the slanted face of the optical probe and muscle fibers by ensuring the optical path difference across surfaces was close to zero. It should be understood that the use of the systems and methods described herein may be used in vivo and do not require the measures used in this experiment.

In an embodiment, the probe 250 comprises a single mode fiber patch cable terminated with angled plain connectors, illuminated muscle fibers and collected reflected power. The optical circulator 200 directs supercontinuum source illumination through the probe 250. The muscle 150 reflects the light from the probe 250 back through the probe 250 and back into the optical circulator 200, which propagates the reflected light into an optical spectrum analyzer (OSA) 300. The analyzer 300 may be model AQ6375 offered by Yokogawa (Japan) or another appropriate model. As shown in FIG. 4B, the analyzer 300 measures reflected power spectra. In an embodiment, the analyzer 300 measures the supercontinuum spectroscopy system output before and after wavelength division multiplexing. The analyzer 300 may have a display that indicates information about the supercontinuum spectroscopy system output. In an embodiment, if the probe 250 is not properly aligned with the muscle 150, then light reflected from the muscle 150 will not couple into the probe 250 and the display on the analyzer 300 will so indicate. Once the probe 250 is properly aligned with the muscle 150, then the reflection from the muscle 150 will begin to couple into the probe 250 and the display on the analyzer 300 will update accordingly. In an embodiment, the laser source 410 is operated for approximately one second once the probe 250 is properly aligned with the muscle 150, in order to measure sarcomere length. The analyzer 300 may have memory for storing data about the supercontinuum spectroscopy system output and may have a USB or other data transmission system that allows such data to be transmitted to other systems, such as a desktop computer or other computing device, for further analysis. In an embodiment, the analyzer 300 determines the intensity of each wavelength of light it receives through the optical circulator.

The number of sarcomeres measured by RRS in series and in parallel is affected by scattering and beam coupling characteristics of the optical probe. Photon mean free paths in muscle tissue are roughly millimeters in length, whereas the Rayleigh length of the optical probe is at least an order of magnitude shorter. Based upon a myofibril (sarcomere) diameter of 1 μm and beam parameters derived from a 0.14 NA optical probe, it was estimated that approximately 1500 sarcomeres contributed to the RRS signal.

Data from the analyzer 300 may be presented for further processing on a computer system 500, such as a desktop computer or other computing device. In an embodiment, the computer system may execute one or more programs 510 that determines the sarcomere length of the muscle 150 from the information provided by the analyzer 300. In an embodiment, the computer system 500 determines the resonant wavelengths from the information provided by the analyzer 300. The computer program then determines the length of sarcomeres in the muscle 150 on the basis of the resonant wavelengths. The term "computing environment" is used herein to describe the computer system 500 and/or the programs 510 that operate on it. In an embodiment, the computer system 500 uses a lookup table 520 to determine the length of sarcomeres in the muscle 150. The dimensions of the lookup table 520 may be the strength of each peak and its location. The lookup table 520 may be pre-populated on the basis of prior research that has identified resonant wavelengths for sarcomeres of different lengths. Alternatively, sarcomere length may be back-calculated directly from the full spectra provided by the analyzer 300. Verification of the lookup table 520 may be performed by experimentation using other known methods to determine sarcomere length. For example, sarcomere length may be measured by laser diffraction. An example of such measurement follows: Small subsamples may be placed on glass slides and trans-illuminated with a 10 mW He—Ne laser with 633 nm center wavelength. Resulting diffraction patterns illuminated a frosted glass slide, and distances between diffracted peaks were measured with digital calipers. The measurement system can be calibrated using a wire grating with 2.0 μm period. Sarcomere length can be calculated from the distance measurements and calibration; sarcomere length measurement from this system had a typical standard deviation of approximately 60 nm and ranged from 2.36-3.03 μm.

Figure 2B:
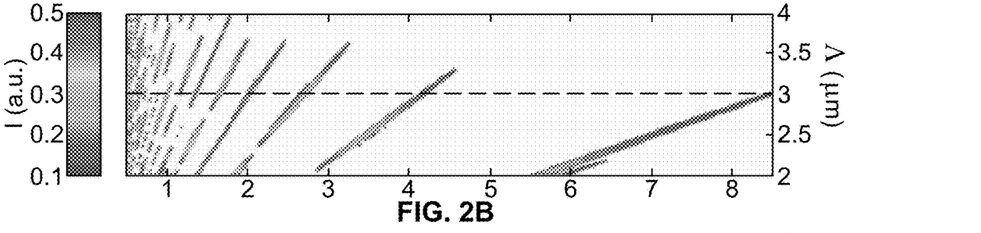
FIGS. 2B-2D illustrate expected reflection efficiency from a physiologically relevant sarcomere length range.
Figure 2C:
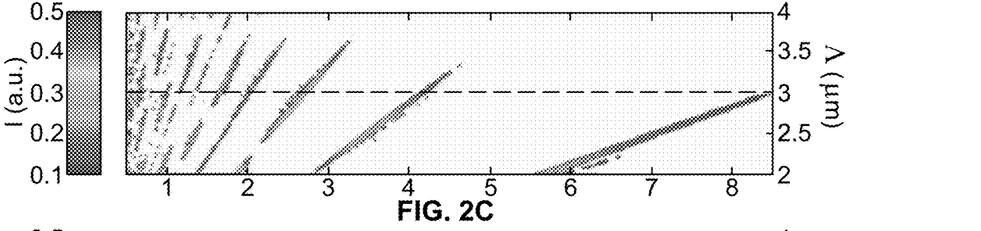
Figure 2D:
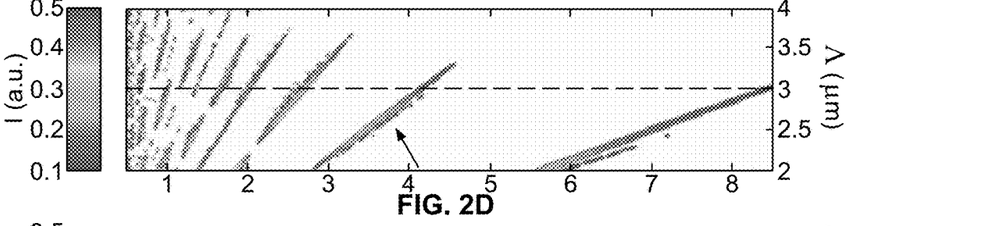

In FIG. 2B, reflection efficiency as a function of illumination wavelength and sarcomere length is represented as a contour plot; a color bar indicates the reflection efficiency. Sarcomere length equal to 3 μm is emphasized with a dashed line for comparison across FIGS. 2B, 2C, and 2D. As expected from Bragg's law, resonant wavelengths appear as lines in contour plots that increase and decrease with sarcomere length, accordingly (FIGS. 2B-D). As expected from Fourier relationships (Eq. 3), reflection efficiencies of resonant orders depend upon order and sarcomere length (FIG. 2B). Further, higher resonant orders are expected to be more sensitive to inhomogeneous sarcomere lengths in series (FIGS. 2C and D).

Figure 2E:
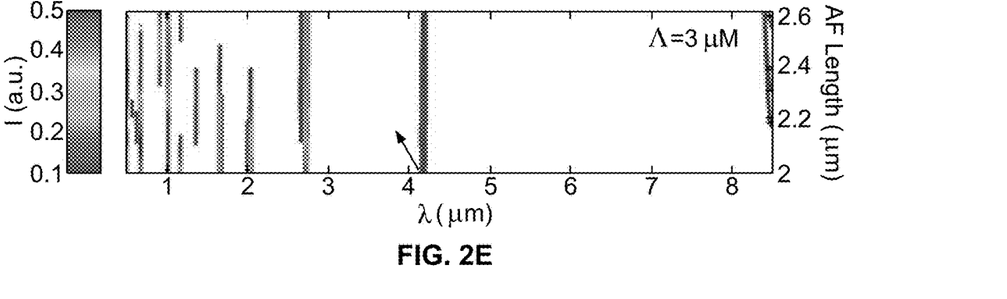
FIG. 2E illustrates how reflection efficiency varies periodically with actin filament length ranging from 1 to 1.3 μm.

In particular, FIG. 2C shows that sarcomere length inhomogeneity among sarcomeres in series introduces speckle-like effects in the reflection efficiency spectrum. FIG. 2D illustrates how a 10° tilt between illumination and sarcomere long axis in the presence of a sarcomere length inhomogeneity causes a slight left shift in resonant wavelengths, i.e., oblate sarcomeres introduce skew to the spectral fingerprint; 12 nm was typical in a wavelength range 1 to 2 μm. So a 10° tilt of the probe, which is recognizable experimentally, would result in less than 25 nm short-estimate of sarcomere length (Eq. 1) for the wavelength ranges used herein; thus tilt effects are likely less than natural sarcomere length variability. Still, tilt was minimized in the example experiments described. FIG. 2E illustrates how reflection efficiency varies periodically with actin filament length ranging from 1 to 1.3 μm (see also Eq. 3), which is an important consideration when considering different muscles and species. The grating region is twice the actin filament length due to actin spanning both sides of the z-band.

In an example use of the system, two resonant wavelengths were measured in eight of ten muscles. In one muscle, a single resonant wavelength was present within the measurement window, which is consistent with theory for particular sarcomere lengths (see above). In another muscle, three resonant wavelengths were measured. Sarcomere lengths were calculated using the following procedure. First, one measured resonant wavelength was used to generate a set of possible sarcomere lengths based upon varying harmonic orders. Then, the measured spectrum was compared to predicted spectral "fingerprints" to identify possible sarcomere lengths, using the lookup table 520.

Sarcomeres within real muscles are not homogenous. After solving for resonant orders using the procedure described above, sarcomere length may be calculated for each measured resonant wavelength to account for natural variability. These sarcomere length estimates may be averaged to generate the sarcomere lengths presented for muscle 150.

Isometric Force Measurements.

To quantify structural and functional damage associated with the probe, isometric force of rabbit tibialis anterior (TA) muscles (N=7 muscles, 4 rabbits) was measured before and after insertion of a prototype intramuscular lensed optical probe (OZ Optics, Canada). TA muscles were chosen for accessibility and availability of reference data. Isometric force measurement and animal preparation followed previously-described methods, but the anterior compartment of the leg was left intact. Briefly, anesthesia was induced with a subcutaneous injection of ketamine/xylazine cocktail (35 and 5 mg/kg respectively) and maintained with 2% isofluorane (2 L/min). Heart rate, blood oxygen saturation (PhysioSuite, Kent Scientific Corp., Torrington, Conn.) and respiratory rate were monitored during all tests. Physiological temperature and moisture were maintained throughout the experiment.

The TA and peroneal nerve were surgically exposed, and the hind limb immobilized in a custom made jig. The distal TA tendon was transected, released from the retinaculum, and clamped at the muscle-tendon junction to a servomotor (Aurora Scientific Inc., Canada). Force generation axes of the TA and servomotor were carefully aligned. Extensor digitorum longus tendon was cut to limit lateral force transmission. A cuff electrode (Model S48, Grass Instruments, Quincy, Mass.) provided direct stimulation to the peroneal nerve. Supramaximal excitation voltage and optimum fiber length were measured experimentally for each TA using twitch contractions. Once these baseline conditions were established, isometric force from tetanic contractions was measured twice before and twice after probe insertion (5 V typical, 0.3 ms pulse width, 100 Hz frequency, 640 ms duration) with two-minute rest between contractions.

Probe insertion was performed with the following procedure. An optical probe was threaded into but not extended past the tip of a 22 gauge hypodermic needle; the needle was inserted approximately 1 cm into the mid-belly of the TA, parallel to muscle fibers. While holding the optical probe in place, the hypodermic needle was removed from the muscle before stimulating contractions. In three animals, the procedure was repeated for the contralateral limb. After contractions, the probe was removed and inspected for damage. No probes were damaged using this protocol.

To determine the structural damage induced by probe insertion, TA muscles were excised and pinned to cork at resting length. An optical probe was re-inserted into the muscle distal to the first insertion point, but otherwise following the same procedure. Then, muscle and probe were flash frozen. Probes were carefully removed just before sectioning, though three probes broke during removal and corresponding muscles were not counted in further analysis. Cross-sections were taken from flash frozen muscles (N=4) at 70 µm thickness using a cryostat (Microm HM500, Waldorf, Germany). This thickness was found to best maintain the integrity of probe induced holes, although it was thicker than the optimal value needed for muscle morphology. Sections were stained with hematoxylin and eosin (H&E) for visualization and imaged with a light microscope (Model DM6000, Leica Microsystems Inc., Buffalo Grove, Ill.). Area fraction of probe-induced damage was calculated using ImageJ.

Referring to FIGS. 3A-3D, it is seen that sarcomere refractive index profile follows protein density. In particular, sarcomere structure was modeled as a quasi-periodic supergrating, which can be seen in electron micrographs (See FIG. 3A, which shows an electron micrograph of sarcomeres at 3.0 µm sarcomere length (A) and which clearly shows the sarcomere protein framework, including actin and myosin filament regions). Values were used as adapted from other sources, to model the sarcomere refractive index profile. Active cross bridge cycling and skeletal muscle rigor were not included in this model because they change refractive index by less than a tenth of a percent.

Figure 3A:
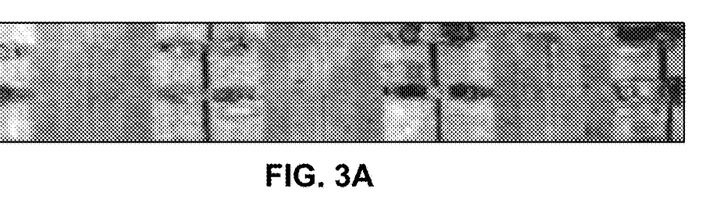
FIGS. 3A-3D illustrate how sarcomere refractive index profile follows protein density.
Figure 3B:
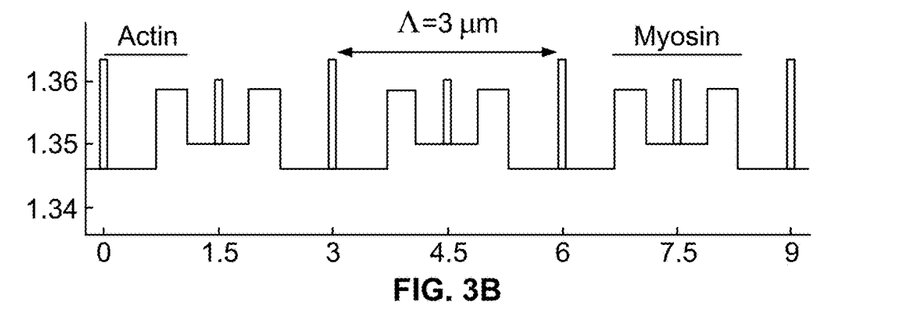
Figure 3C:
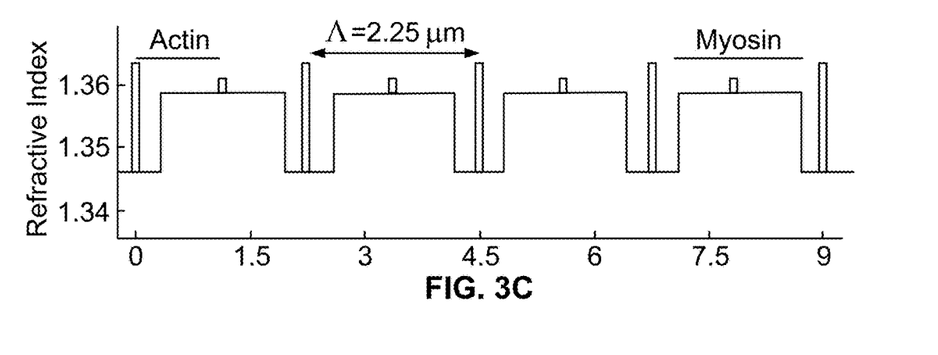
Figure 3D:
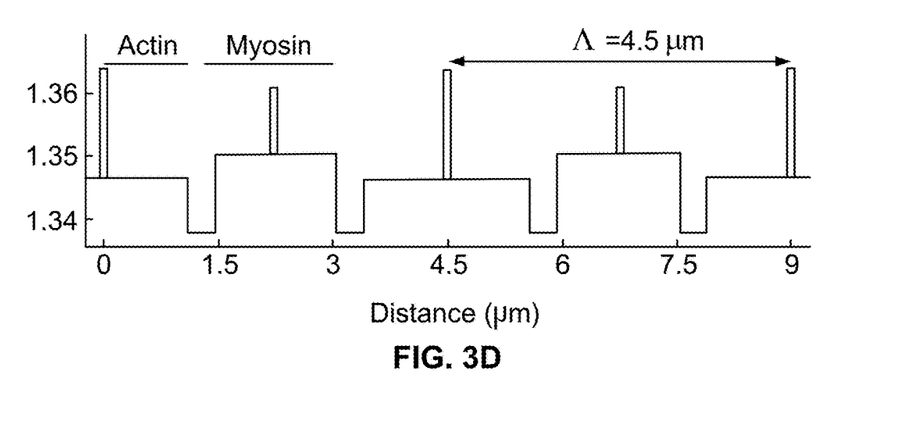

Close examination of the sarcomere model reveals that the refractive index profile is actually a superposition of the refractive indices of four principal protein regions: m-line, z-band, myosin filaments, and actin filaments. Widths of z-band and m-line regions were 50 nm. Myosin filament length was 1.6 µm. Actin filament length was 1.1 µm unless stated otherwise. Phase of each region was matched to the sarcomere structure. Refractive index for baseline, z-band, m-line, myosin, and actin regions were 1.3473, 0.0272, 0.0200, 0.0227, and 0.0187. Importantly, overlap between actin and myosin filaments changes with sarcomere length, and refractive index profiles are adjusted accordingly. See, e.g., FIGS. 3 B-D, which depicts refractive index profiles corresponding to varied sarcomere lengths (note dramatic changes in refractive index profile appearance as a function of sarcomere length).

Simulation.

A one-dimensional multi-layer rigorous coupled wave analysis (RCWA) was used to simulate reflection spectra from sarcomeres. RCWA is a widely used method for analyzing diffracting structures. Here, a simple 1D multi-layer RCWA implemented in Matlab was used to predict reflected laser diffraction from sarcomeres. Index of refraction values were slightly adapted from literature. Briefly, RCWA is a semi-analytical method in which periodic structures are decomposed into many layers with uniform index of refraction. Maxwell's equations are expanded by Floquet functions and a computer solves for forward and backward propagating waves. RCWA was used to calculate reflection efficiency, plotted as relative intensity, at each wavelength and sarcomere length presented. Rather than hold sarcomere number constant, in the experiments a constant length of 50 µm was used to approximate the experimental system's Rayleigh length divided by two to accommodate forward and backward paths. The illumination was collinear to sarcomeres for all simulations discussed. Sarcomere inhomogeneity was simulated by randomly varying sarcomere length for each sarcomere in series. Sarcomere length variation followed white Gaussian noise, and standard length deviations were set to approximately 60 nm to match standard deviations in sarcomere length measured by laser diffraction. All analyses were performed in MATLAB (The MathWorks, Inc., Natick, Mass.).

Statistical analysis. Linear correlations were performed in MATLAB (The MathWorks, Inc., Natick, Mass.) and data points were treated as independent samples. A paired t-test was performed to compare average isometric force before and after probe insertion using Prism software (GraphPad, San Diego, Calif.). Power analyses were performed using G*Power 3.1 (35) (Heinrich Heine University Dusseldorf, Germany). Significance level was set to 0.05 for all tests.

Results. Experimental data from the system 400 confirms that the system 400 is able to accurately measure sarcomere length. In testing, the system 400 was used to collinearly illuminate muscle fibers with known sarcomere length, and reflection intensity was measured as a function of wavelength. The reflection data was compared to mathematical predictions that relate sarcomere structure to expected signal spectra. In particular, measured RRS spectra was compared to predicted RRS spectra from idealized sarcomeres, and sarcomere lengths were compared as measured by RRS and LD. From these comparisons, it was concluded that RRS successfully captures sarcomere length. In particular, all measured Bragg wavelengths matched the slightly adjusted simulated predictions by less than 2%, which suggests the system 400 may be used to accurately measure sarcomere length. Additionally, in tests, using the supercontinuum spectroscopic system 400 (or system 400, for short), close agreement is seen between sarcomere lengths measured by resonant reflection spectroscopy and laser diffraction in an ensemble of ten distinct muscles.

Figure 5A:
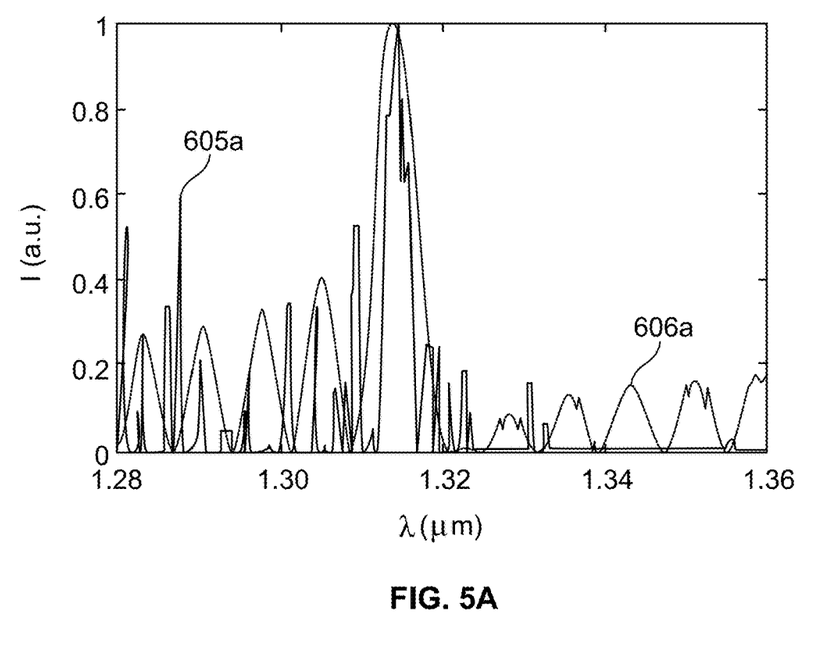
FIGS. 5A-5D illustrate how the theory for sarcomere refractive index accurately models reflected signals across the tested muscles.
Figure 5B:
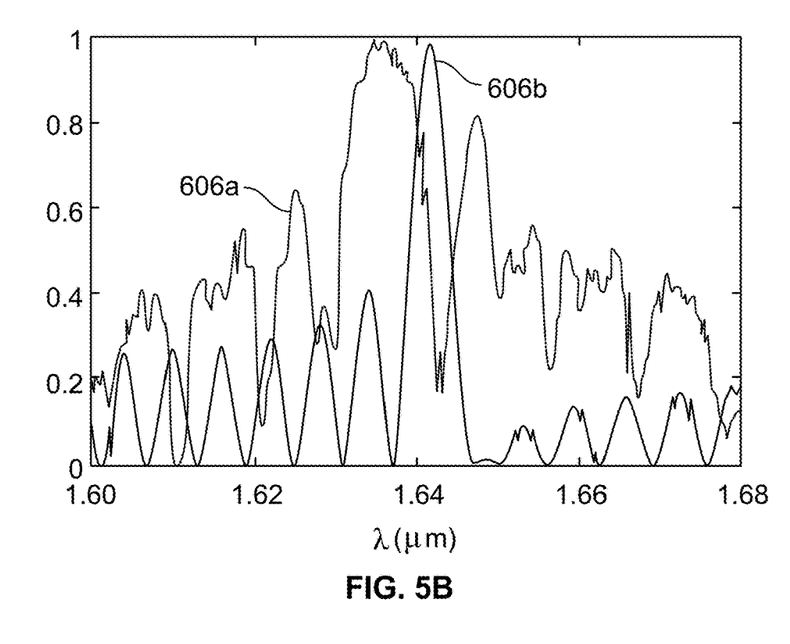

To test the model, multiple resonant orders from muscles of known sarcomere length were measured using the new supercontinuum spectroscopy system and then compared to numerical simulations. In ten muscles, experimental measurements agreed remarkably well with simulations. In particular, FIGS. 5A and 5B illustrate an overlay of unprocessed reflected power (plots 605a and 605b) and theoretical simulations (plots 606a and 606b) from muscle tissue with sarcomere length 2.45 μm and which exhibit agreement. Importantly, the resonant wavelengths, which have the strongest reflections, match extremely well for both the $4_{th}$ (B) and $5_{th}$ (A) order. In this example, the average difference between simulated resonant wavelength from idealized sarcomeres and experimental measurements was 3.5 nm, which equates to a 6.5 nm sarcomere length or 0.27% uncertainty. Furthermore, the reflection spectrum approximates a superposition of sinc functions as predicted by the theoretical model. Notably, the period of oscillations in measured spectra roughly match the predicted period.

Figure 5C:
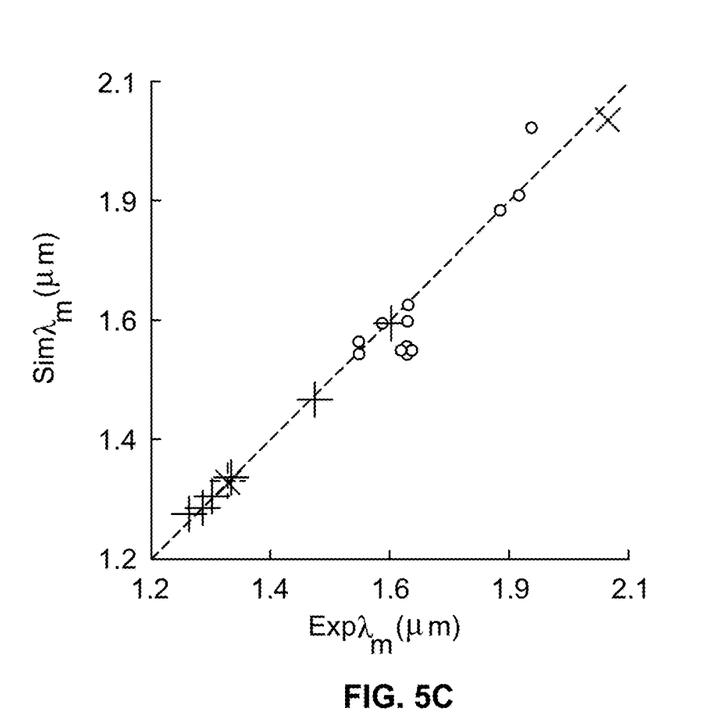
Figure 5D:
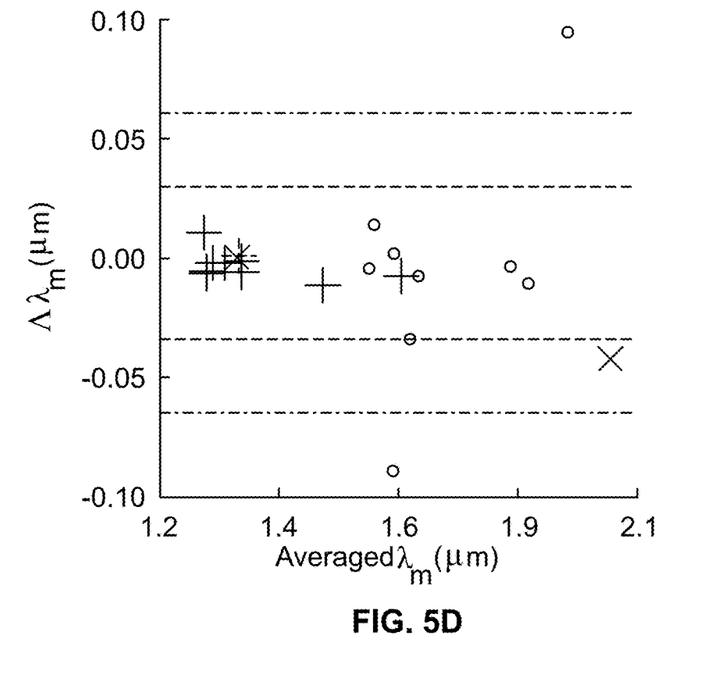

Experimental measurements match well across the entire sample, which includes a range of sarcomere lengths from 2.36 to 3.03 μm. This dataset revealed a significant correlation (p<0.001) between experimentally measured and simulated resonant wavelengths with the theoretical model explaining 98% (R2=0.984) of the variability in experimental measurements (FIG. 5C). That is, experimentally measured and simulated resonant wavelengths ($\lambda_m$) for $3_{rd}$ order (represented in FIG. 5 with an "X"), $4_{th}$ order (represented with a dot), $5_{th}$ order (represented with a "+"), and $6_{th}$ order (represented with a "*") significantly correlate ($R_2$=0.984, p<0.001) across muscle samples. The dashed line represents line of unity. As a further test, an agreement plot was generated to visualize the fit between data sets (FIG. 5D). Agreement plots are not visually biased by scale as can occur with correlations. Thus, an agreement plot presents an unbiased view of variability in differences (Δλm) between simulated and experimentally measured resonant wavelengths. Dashed lines represent standard deviation and twice the standard deviation. There is no systematic bias between modeled and experimentally measured resonances (P=0.86). In the agreement plot, it was seen that that two of the ten muscles are less accurately modeled by idealized sarcomeres. Currently, sufficient data is lacking to conclude the cause of disagreement in these muscles, but it is hypothesized, based upon numerical simulations, that the shifts are caused by radial and/or longitudinal sarcomere length inhomogeneity. Nonetheless, these shifts do not prevent sarcomere length measurements, as seen in the next section.

Sarcomere Length Measured by Laser Diffraction Vs. Resonant Reflection Spectroscopy.

Figure 6A:
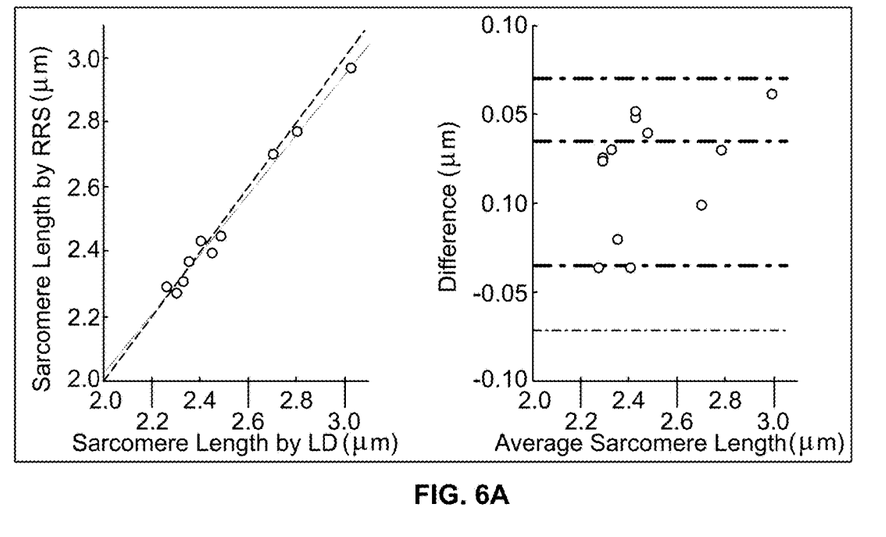
FIGS. 6A-6B illustrate correlation of sarcomere lengths measured by different techniques as well as an agreement plot.
Figure 6B:
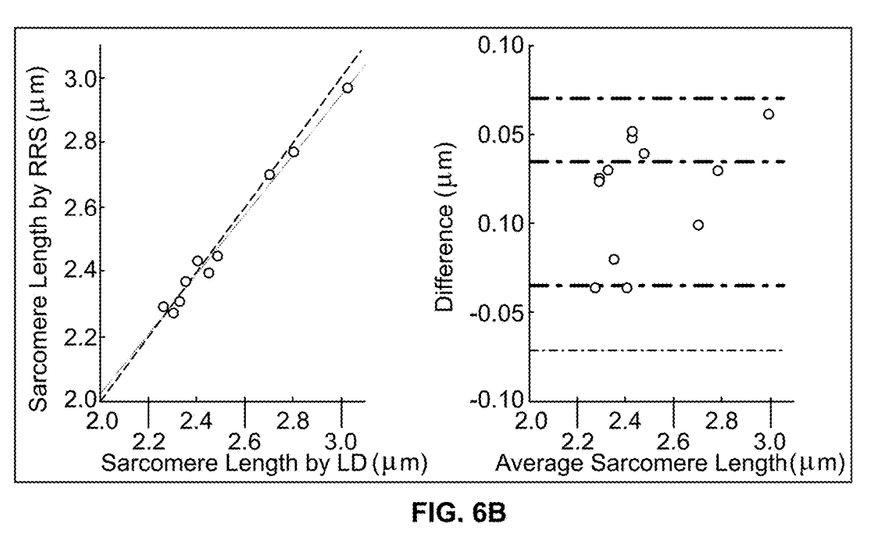

Using the procedure described above, sarcomere length from RRS measurements was calculated. Sarcomere length measured by LD and RRS were highly significantly correlated (R2=0.984, p<0.001) (FIG. 6A). The dashed line represents line of unity. The dotted line represents line of best fit. Variability between measurement methods is more clearly seen in an agreement plot (FIG. 6B). Differences between method sarcomere length measurements were not significantly correlated across sarcomere length (P=0.16), indicating sarcomere lengths measured by RRS are not systematically biased (80% power to detect 1.7 nm/μm skew). Even with a one-dimensional and idealized sarcomere model, sarcomere lengths measured by RRS and LD agree with a standard deviation of ±35 nm (FIG. 6B), well within a physiologically-meaningful tolerance.

Muscle Function after Intramuscular Insertion of Optical Probes.

Figure 7A:
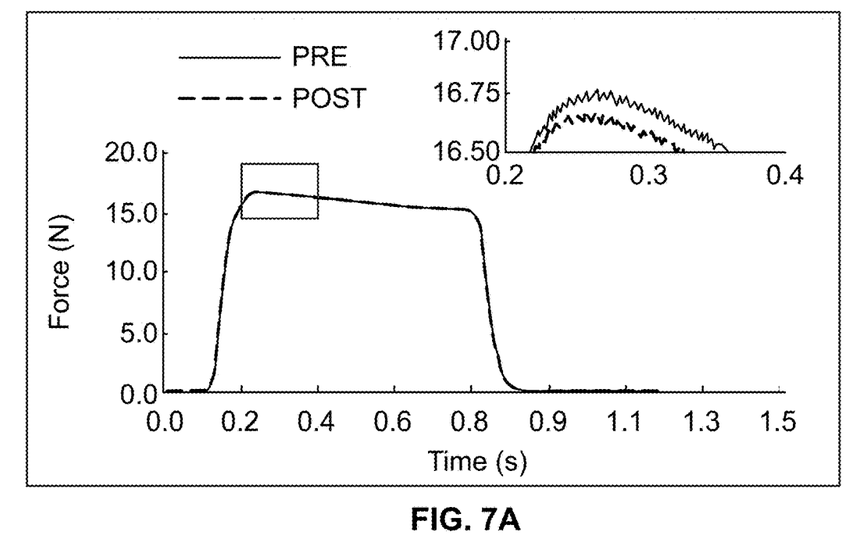
FIGS. 7A-7C illustrate how insertion of an optical probe has little effect on structure or function.
Figure 7B:
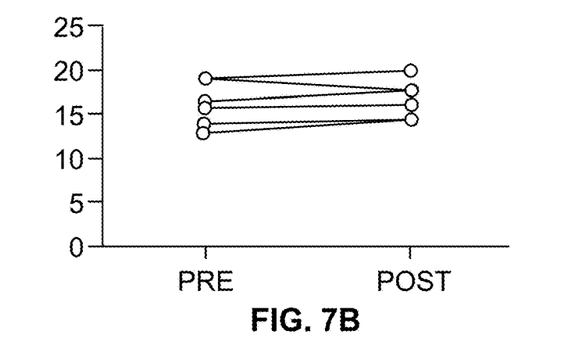
Figure 7C:
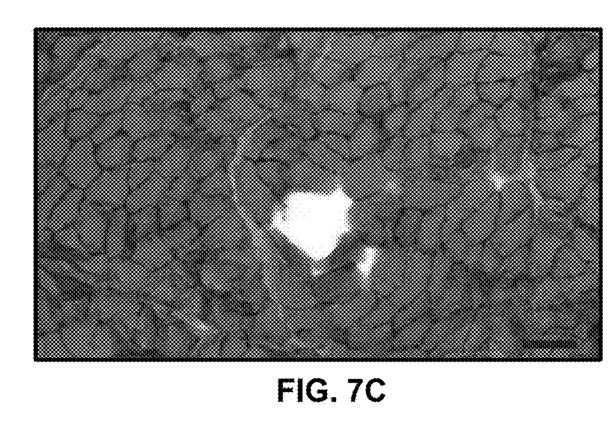
Figure 8:
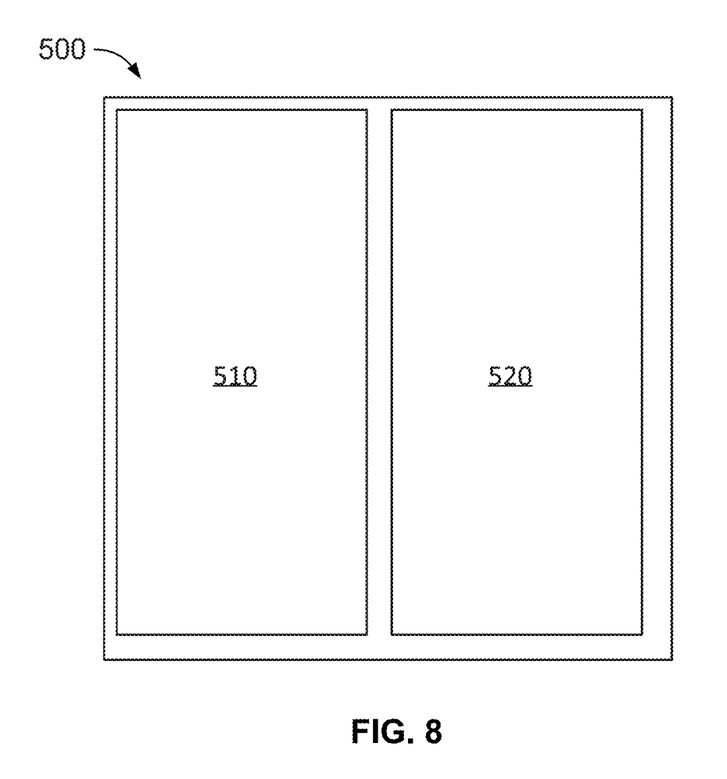
FIG. 8 illustrates a schematic of a computing environment.

Future RRS applications may require intramuscular insertion of optical probes. To assess the amount of muscular damage induced by probe insertion, maximal isometric contractile force in rabbit TA muscles was measured before and after prototype lensed optical probe insertion (FIGS. 7A and B). As may be seen, there was almost no change in contractile force with probe insertion. That is, insertion of an optical probe has almost no effect on structure or function. FIG. 7A shows a representative isometric contractile record of a rabbit TA pre- and post-insertion of an optical probe. The inset shows the force record enlarged at the plateau. FIG. 7B (Paired t-test) shows that isometric muscle function is not significantly different after probe insertion (P=0.213), i.e., averaged pre-insertion and averaged post insertion forces were not significantly different. Power analysis indicated an 80% power to detect a 5% force change given the experimental variability. To assess the structural damage caused by probe insertion, corresponding cross-sections of rabbit TA muscles stained with H&E (FIG. 7C) were examined. FIG. 7C shows a representative 70 μm thick cross-section of a rabbit TA muscle stained with hematoxylin and eosin, which shows an area of probe insertion. The damaged muscle area fraction, calculated as area of damage divided by muscle cross-sectional area, associated with probe insertion, was found to be 0.078%. Taken together, these data suggest that optical probe insertion into muscle has almost no effect on structure or function. The scale bar represents 0.1 μm.

This study demonstrates two key points: theoretical development of RRS and experimental assessment of its ability to measure sarcomere length. RRS can potentially enable critically-important sarcomere length measurements in vivo, in real time, and in humans because the information is encoded in optical wavelengths rather than spatial information as is the case in current techniques. Using a new supercontinuum system and a one-dimensional sarcomere refractive index model, it was demonstrated that sarcomere lengths measured by RRS agree remarkably well with sarcomere lengths measured by LD, a standard technique. Thus RRS is theoretically feasible, though several key points differentiate the feasibility system used here and the desired in vivo RRS technique. A number of considerations are raised in the following discussion, but still, the idealized model of sarcomeres explained 98% of the variability in the key information contained in measured RRS spectra.

First, an extra-muscular probe was used in the feasibility experiment. This allowed the exploration of illumination angles to align illumination with the long axes of sarcomeres and provide confidence relating the theoretical model with experimental geometry. Severely oblique sarcomeres would have demanded data collection and alignment tests beyond the scope of this initial feasibility study. A future intramuscular probe may not have control of illumination angles and it may be preferable to employ additional redundant measurements to address this added level of complexity. However, simulations of 10° oblique sarcomeres caused skew in the spectral fingerprint that would change sarcomere length estimates by less than 25 nm. Additionally, intramuscular probes impose geometric changes to the local muscle fibers, though these changes appear small in histological analysis.

Second, chemically fixed muscles were used for RRS measurements while the true benefit of RRS is in in vivo use. Using fixed muscles allowed the prototyping of the experiments while minimizing the animals needed for this study. Importantly, it has been demonstrated that fixation does not systematically introduce errors in sarcomere length measurements by LD. Signal generation in RRS and LD are fundamentally similar, though the geometry is different, so it is unlikely that fixation dramatically confounded the results. Fixation, though, may systematically change baseline refractive index compared to fresh muscle sarcomeres. This may cause a corresponding shift to measured sarcomere lengths. Refractive indexes used here led to RRS measured sarcomere lengths to match those measured by LD in fixed muscles, though a baseline shift may be implemented for in vivo use.

Third, in vivo measurements are associated with natural movement. Motion artifacts are a confounding factor present in microendoscopy measurements of in vivo sarcomere length because the technique operates at only a few Hz. RRS, however, does not require point scanning and can operate at many kHz rates. Thus, motion artifacts will not confound sarcomere length data collected by RRS. If index of refraction changes during contraction are minimal or can be resolved, RRS may offer a unique capability to even distinguish between passively and actively contracting muscle, in vivo.

Last, several other factors may systematically affect RRS signals and may be considered in other various embodiments of the systems and methods described herein. These include concentration changes in non-contractile organelles, such as mitochondria and nuclei, may affect the base level refractive index and systematically shift sarcomere lengths shorter or longer. It is expected, however, that the magnitudes of these effects will be buried by variability caused by within-muscle sarcomere length heterogeneity. The also include length changes to z-band or actin filament regions, which can affect the sarcomere refractive index profile and are expected to affect the relative intensities of resonant orders.

What is claimed is:

1. A method of measuring muscle sarcomere length, comprising:
    a. illuminating a set of muscle fibers with electromagnetic radiation;
    b. measuring an intensity of the electromagnetic radiation in a wide spectrum that crosses at least two resonant orders as reflected from the muscle fibers, the measuring occurring as a function of wavelength;
    c. determining one or more wavelengths corresponding to maximums of reflected intensity; and
    d. correlating the one or more determined wavelengths with an average muscle sarcomere length for the set of muscle fibers to obtain a measurement of the set of muscle fibers.

2. The method of claim 1, wherein the illuminating includes illuminating with a supercontinuum source.

3. The method of claim 2, wherein the supercontinuum source provides a wavelength range of 1250 to 2050 nm.

4. The method of claim 1, wherein the illuminating includes illuminating in a collinear fashion.

5. The method of claim 1, wherein the illuminating and measuring is performed by a resonant reflection spectroscopy system.

6. The method of claim 5, wherein the resonant reflection spectroscopy system comprises a non-linear fiber.

7. The method of claim 1, wherein the determining further comprises determining a single measured resonant wavelength falling in a wavelength band.

* * * * *